United States Patent [19]
Sprinkel, Jr.

[11] Patent Number: 5,261,424
[45] Date of Patent: Nov. 16, 1993

[54] CONTROL DEVICE FOR FLAVOR-GENERATING ARTICLE

[75] Inventor: F. Murphy Sprinkel, Jr., Glen Allen, Va.

[73] Assignee: Philip Morris Incorporated, New York, N.Y.

[21] Appl. No.: 709,023

[22] Filed: May 31, 1991

[51] Int. Cl.⁵ .............................. A24D 1/00
[52] U.S. Cl. ............................ 131/329; 131/271; 131/273; 128/202.21; 128/203.26; 128/203.27; 128/204.21
[58] Field of Search ............ 131/329, 271, 273; 128/202.21, 203.26, 203.27, 204.21

[56] References Cited

U.S. PATENT DOCUMENTS

| | | | |
|---|---|---|---|
| 3,881,059 | 4/1975 | Stewart | 434/185 X |
| 4,068,672 | 1/1978 | Guerra | 131/170 A |
| 4,446,747 | 5/1984 | Kamm | 73/862.58 |
| 4,735,217 | 4/1988 | Gerth et al. | 131/273 |
| 4,922,901 | 5/1990 | Brooks et al. | 128/203.26 |
| 4,947,874 | 8/1990 | Brooks et al. | 131/329 |
| 4,947,875 | 8/1990 | Brooks et al. | 131/330 |
| 5,060,671 | 10/1991 | Counts et al. | 131/329 |

FOREIGN PATENT DOCUMENTS

| | | |
|---|---|---|
| 0295122 | 12/1988 | European Pat. Off. . |
| 0358002 | 3/1990 | European Pat. Off. . |
| 0358114 | 3/1990 | European Pat. Off. . |

Primary Examiner—V. Millin
Assistant Examiner—J. Doyle
Attorney, Agent, or Firm—James P. Bergin

[57] ABSTRACT

A control device for electrically heated flavor generators. Sensors detect user lip activity associated with taking a draw and trigger heating of flavor-generating materials.

65 Claims, 7 Drawing Sheets

CONTROL DEVICE FOR FLAVOR-GENERATING ARTICLE

BACKGROUND OF THE INVENTION

1. Field of the Invention

The present invention relates to a control device for an article wherein flavor-generating materials are heated to release tobacco flavors. More particularly, it relates to a device adapted to initiate heating of the flavor-generating material.

2. Description of Related Art

Flavor-generating articles generally are known in the art. In such articles, flavor beds of tobacco or tobacco-derived material are heated to release tobacco flavors without producing all the normal products of tobacco combustion. In some such devices, a combustible heat source is used to heat air which is then drawn past a bed of flavor-generating material to heat the material and thereby release the tobacco flavor. In other such devices, the flavor-generating material is heated electrically.

In the above-described devices, the user initiates heating of the flavor-generating material by drawing air into his mouth. In the case of the combustible heat source device, the air is drawn through or around the heat source and then past a bed of flavor-generating material to heat the material. For the electrical heat source device, the user's draw is detected by a pressure or air flow sensor, which in turn initiates heating of the flavor-generating material.

In the flavor generators described above, there occurs between the start of the draw and the release of flavor from the flavor-generating material a substantial lapse of time, as compared to that which occurs in conventional cigarettes. Users find this lag time to be a negative attribute of such flavor generators. Another problem with current flavor generators is that some users do not draw air for a long enough period of time to permit full release of the flavor materials before the draw is complete. Again, this deficiency in current flavor generators can result in user dissatisfaction.

In electrical flavor generators in particular, various non-draw activities can create an air flow or pressure change within the device to falsely or prematurely initiate the heating sequence. For example, if the user waves the article in his hands or otherwise agitates the device, the heating mechanism may be falsely triggered. Also, if the user talks while holding the article between his lips, the heating mechanism may be falsely or prematurely triggered.

These problems can be avoided by using an entirely different mechanism to control the heating sequence. One proposed mechanism involves the use of a push button device which the user must activate for each draw. This mechanism is itself unattractive, however, because it requires user action substantially different than that practiced by smokers of conventional cigarettes.

Accordingly, it is an object of the present invention to provide a control device for a flavor-generating article that initiates heating of flavor-generating material such that there is only a small lapse of time between the start of the user's draw and the delivery of flavor to the user.

It is also an object of this invention to provide a control device that is resistant to false non-draw air flow or pressure changes.

It is a further object of this invention to provide a control device that responds to the user's normal smoking behavior to initiate heating of the flavor-generating material.

SUMMARY OF THE INVENTION

The present invention has been found to overcome the disadvantages of the prior art and provides an improved device to initiate heating of flavor-generating material. In accordance with the invention, one or more sensors are placed at the tip of the mouthpiece of the flavor generator. These sensors detect physical, chemical, or electrical changes associated with user lip activity, and produce corresponding electric signals. The control device monitors these electric signals, and when the signals reach certain threshold levels, the control device initiates heating of the flavor-generating material.

BRIEF DESCRIPTION OF THE DRAWINGS

The above and other objects and advantages of the invention will be apparent from the following detailed description, taken in conjunction with the accompanying drawings, in which like reference numerals refer to like parts throughout, and in which.

DETAILED DESCRIPTION OF THE PREFERRED EMBODIMENTS

Figure 1:
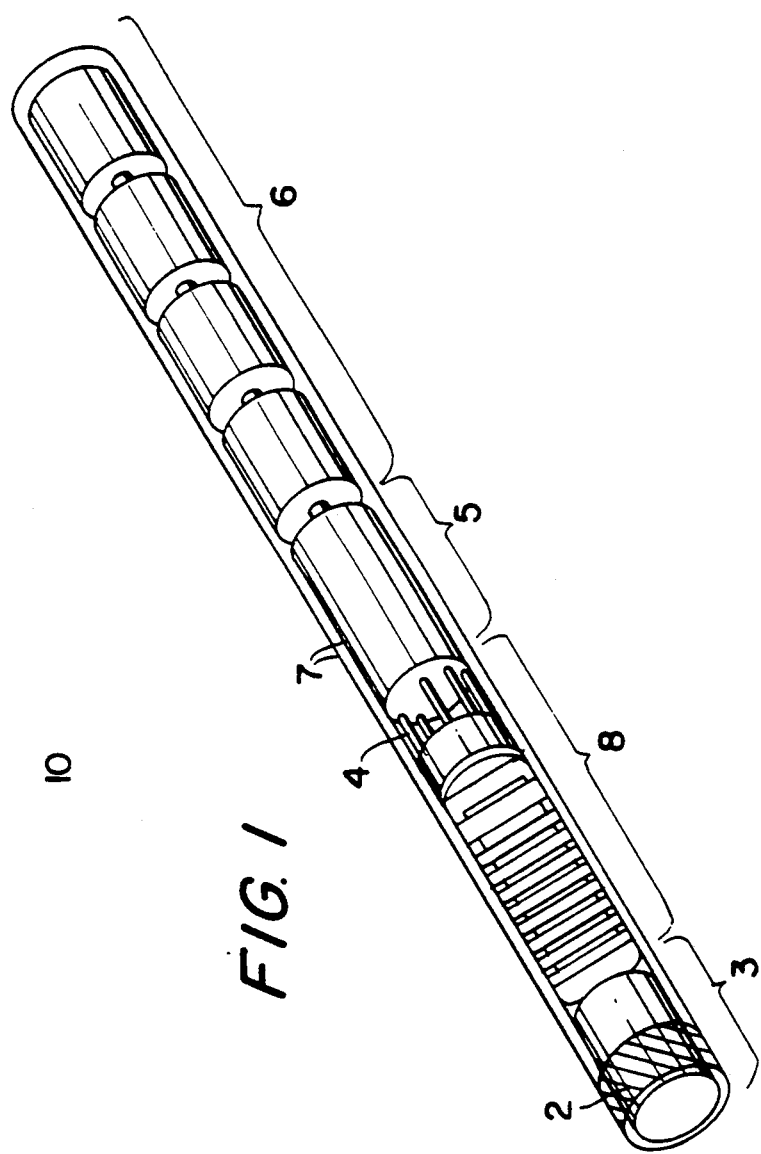
FIG. 1 is a side view of a flavor-generating article, with the control device incorporated at the mouthpiece end, and with several portions of the drawing cut away to show the internal components of the article.

It has recently been found that the actions of a user's lips when drawing on a cigarette are unlike any other activity which occurs when the user is smoking a cigarette. The user applies significantly more pressure on the filter or mouthpiece end of the cigarette when drawing smoke than at any other time. By monitoring with sensors the motor activity of the user's lips when placing pressure to the tip of a flavor generator, it is possible to initiate heating of the flavor-generating material before the user actually starts to draw air through the flavor generator. This reduces the lag time between the start of the draw and the delivery of flavor to the user.

The sensors used at the tip of the flavor generator can take many forms, depending upon how the motor activity of the lips is to be monitored. For example, a pressure sensor, such as a strip of piezoelectric film, can be used to monitor the amount of pressure the user applies to the tip of the flavor generator. The piezoelectric sensor can also be used to detect the change in temperature that occurs when a flavor generator is placed between a user's lips. One film which has been found to be acceptable for such an application is Kynar ® piezo film manufactured by the Pennwalt Corporation.

In addition to monitoring the change in pressure at the surface of the tip of the mouthpiece, it is also possible to detect the start of a draw by measuring the electrochemical activity in the user's lips to detect a change in that activity that corresponds to the start of a puff. To measure this change in electrochemical activity, one can use standard pH electrodes, or electrodes which are sensitive to sodium, calcium, or other ion levels. For these sensors, microchip-mounted membrane electrodes can be used.

Finally, it also is possible to measure the changes in electrical signals associated with the muscular contraction of the lips which accompanies a user's draw. To measure the electrical activity associated with a draw, current-sensing or preferably voltage-sensing chip-mounted electrodes can be used.

As used in this disclosure, the term "flavor generator" refers to a device wherein flavor-generating material is electrically heated to release flavor to a user. Such devices are disclosed in co-pending commonly assigned U.S. patent applications Ser. Nos. 07/444,746 and 07/444,818, both filed on Dec. 1, 1989, and both hereby incorporated by reference in their entirety.

Flavor-generating material can be any material that, when heated, releases a flavor-containing substance. Such materials may include tobacco condensates or fractions thereof, or tobacco extracts or fractions thereof, deposited on an inert substrate. These materials, when heated, generate or release a flavor-containing substance (which may include nicotine) that can be drawn in by the user. The flavor-generating material can also be unburned tobacco or a composition containing unburned tobacco that, when heated to a temperature below its burning temperature, generates or releases a flavor-containing substance. Any of these flavor-generating materials may also include an aerosol-forming material, such as glycerine or water, so that the user has the perception of inhaling and exhaling "smoke" as in a conventional cigarette.

As discussed above, the activity exhibited by a smoker's lips when taking a draw is significantly different than other activities which occur during smoking. One parameter that can be measured is the pressure exerted against the filter. The differences in pressure can be used to generate an electric signal to trigger the heating of a flavor-generating material.

FIG. 1 depicts a flavor-generating article 10 with a piezoelectric sensor 2 attached to the mouthpiece or filter section 3 of the article. A band of piezo film is wrapped around the filter, and electric wires are routed through the filter paper. The piezo sensor signals are routed through the connectors 4 to the control circuits 5. The circuits are powered by a block of batteries 6 at the front-end of the article. The control block 5 houses, among other things, the heater activation control circuit and the piezo sensor signal discriminating control circuit, all described later in the specification. The control block may also house visible heater selection indicators 7, by which the user can visualize how much flavor-generating capacity is remaining in the article. Finally, heater block 8 houses graphitic sequential heaters, which are wrapped in flavor-generating material, and which, when activated, heat the material to release flavors to the user.

The embodiment depicted in the figure is made with a DTI Kynar ® piezo film sensor manufactured by Pennwalt. This piezo film sensor was used to graphically illustrate the signals which were generated by typical lip pressure against the filter of a cigarette. The output of the sensor was applied to the data translation interface of a standard personal computer, and Lab Tech ® notebook software created by Laboratory Technology Corporation of Wilmington, Mass. was used to process and display the data. The data was sampled as analog volts at 5 or 20 Hz versus the internal clock. The system exhibited significant dampening as the normally seen high frequency noise was not present.

Figure 2:
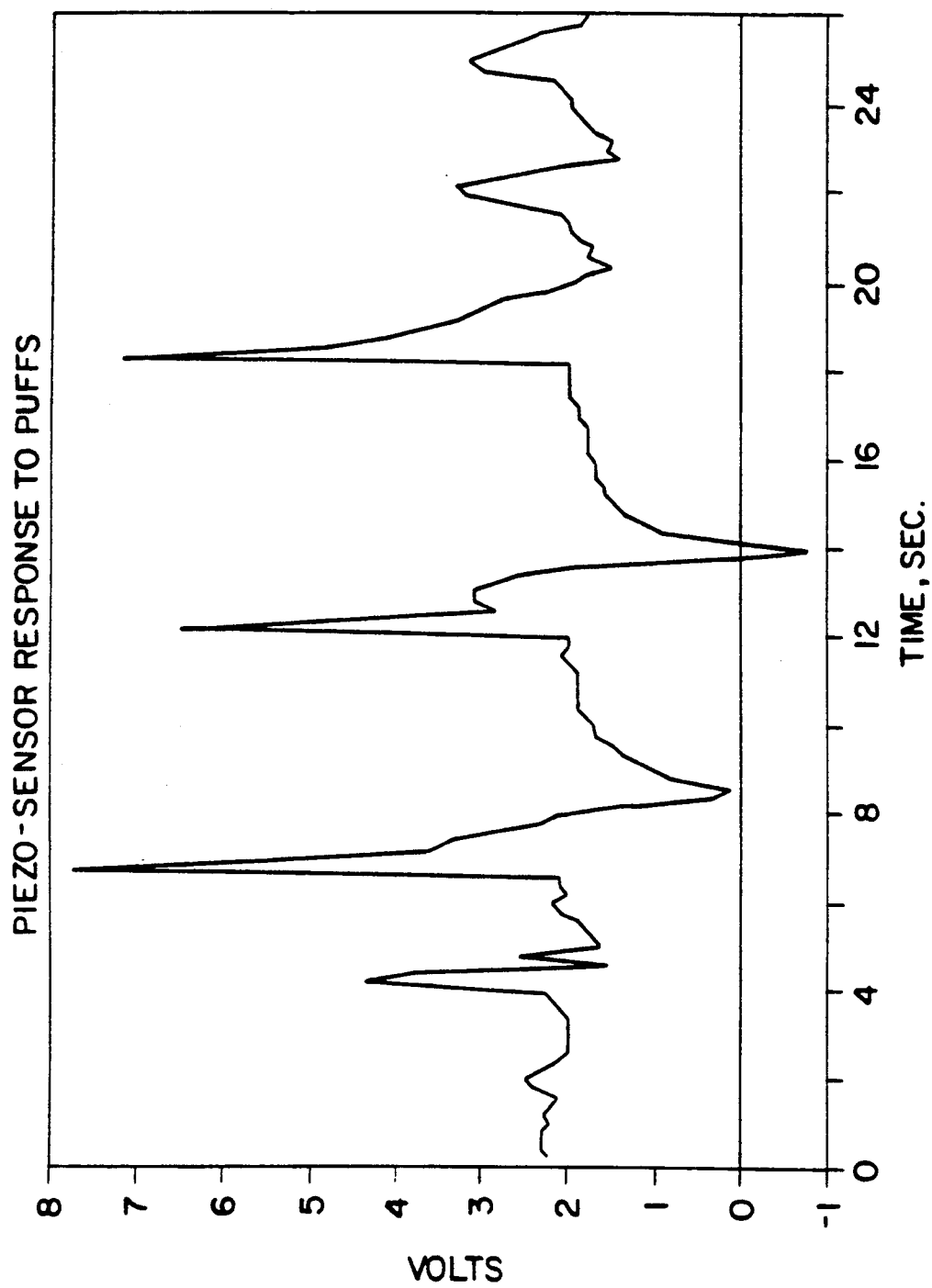
FIG. 2 is a plot of electric signals generated by a sensor of the invention that correspond to user draw and non-draw activity.
Figure 3:
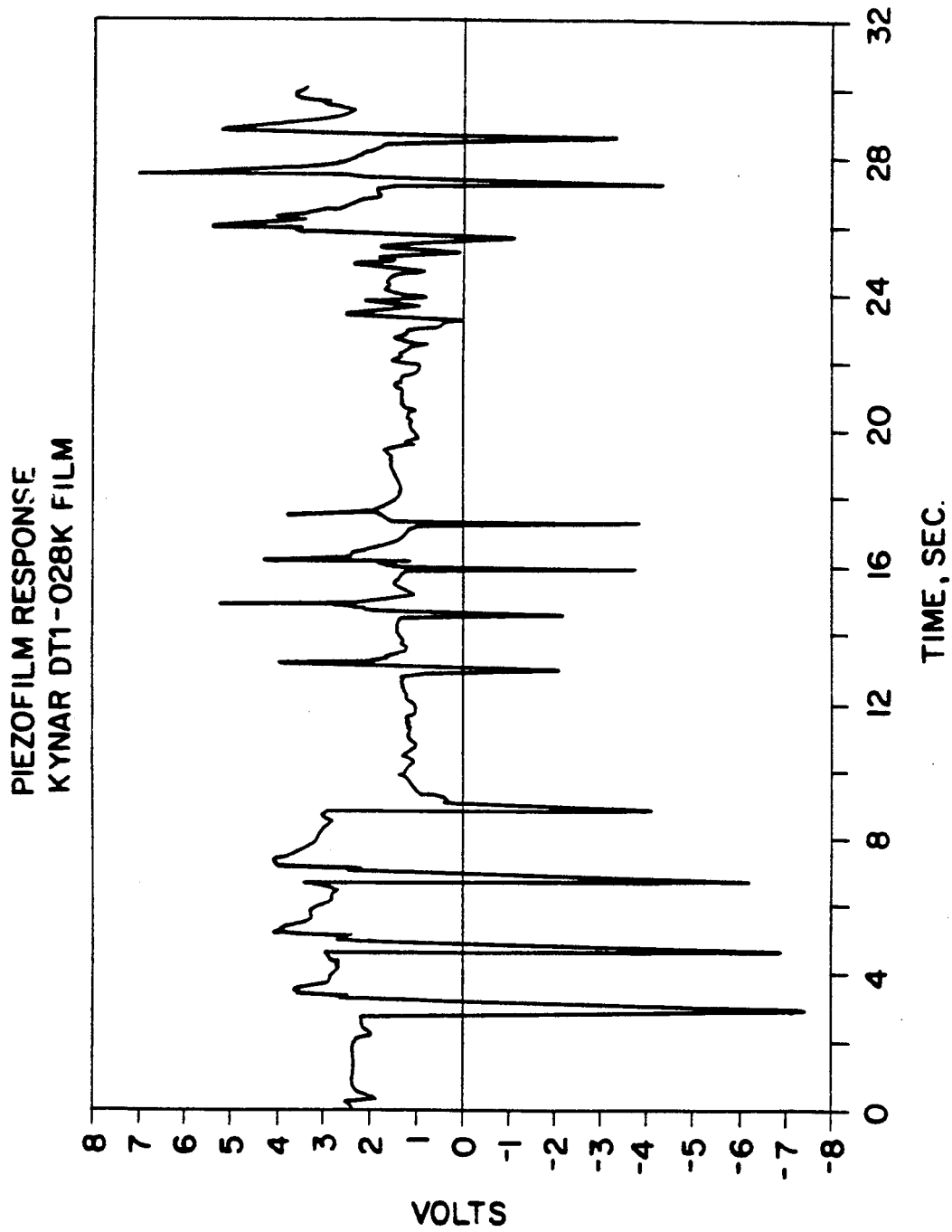
FIG. 3 is also a plot of electric signals generated by a sensor of the invention that correspond to user draw and non-draw activity.
Figure 4A:
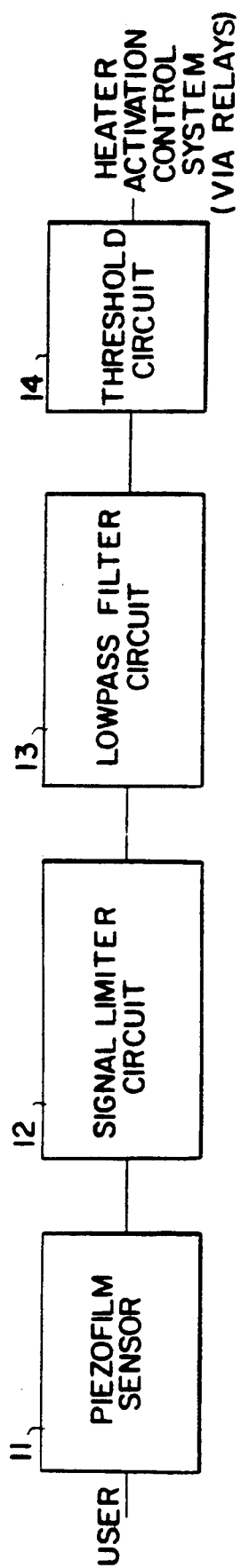
FIGS. 4A and 4B (hereafter collectively "FIG. 4" are functional and circuit-level diagrams of a system used to differentiate between user draw and non-draw signals.
Figure 4A:
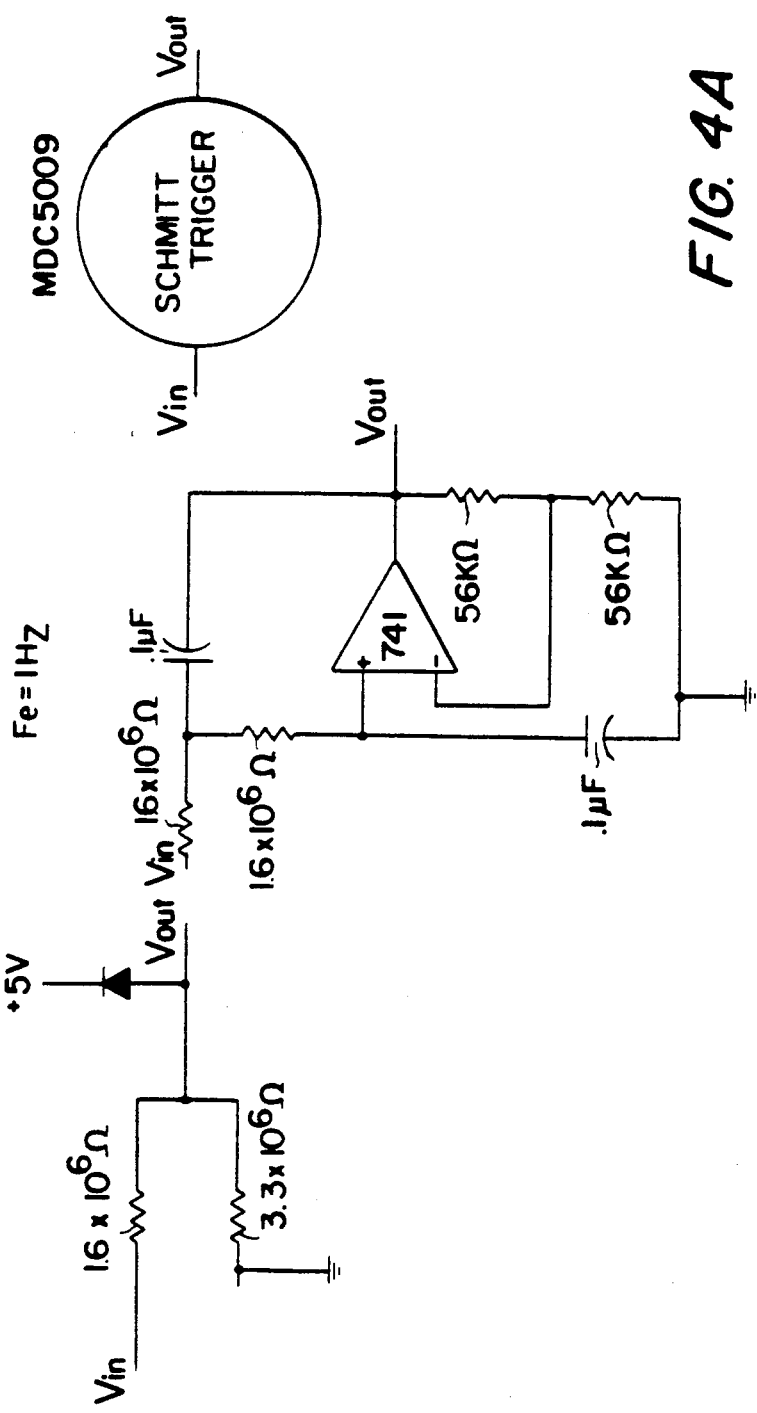
Figure 4B:
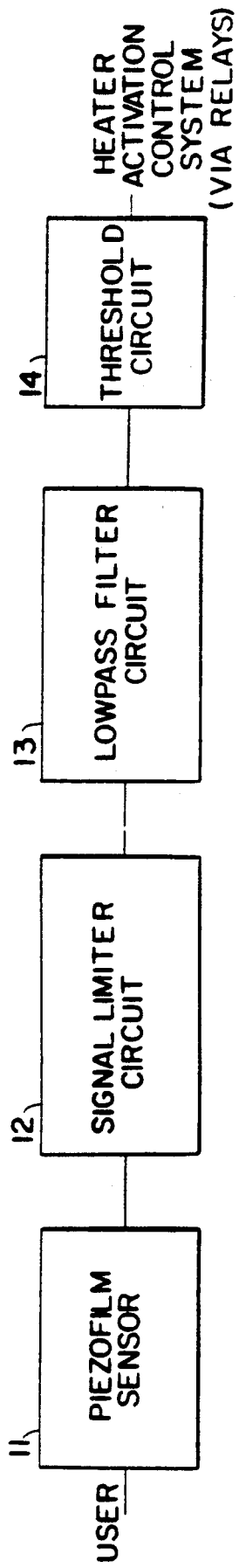
Figure 4B:
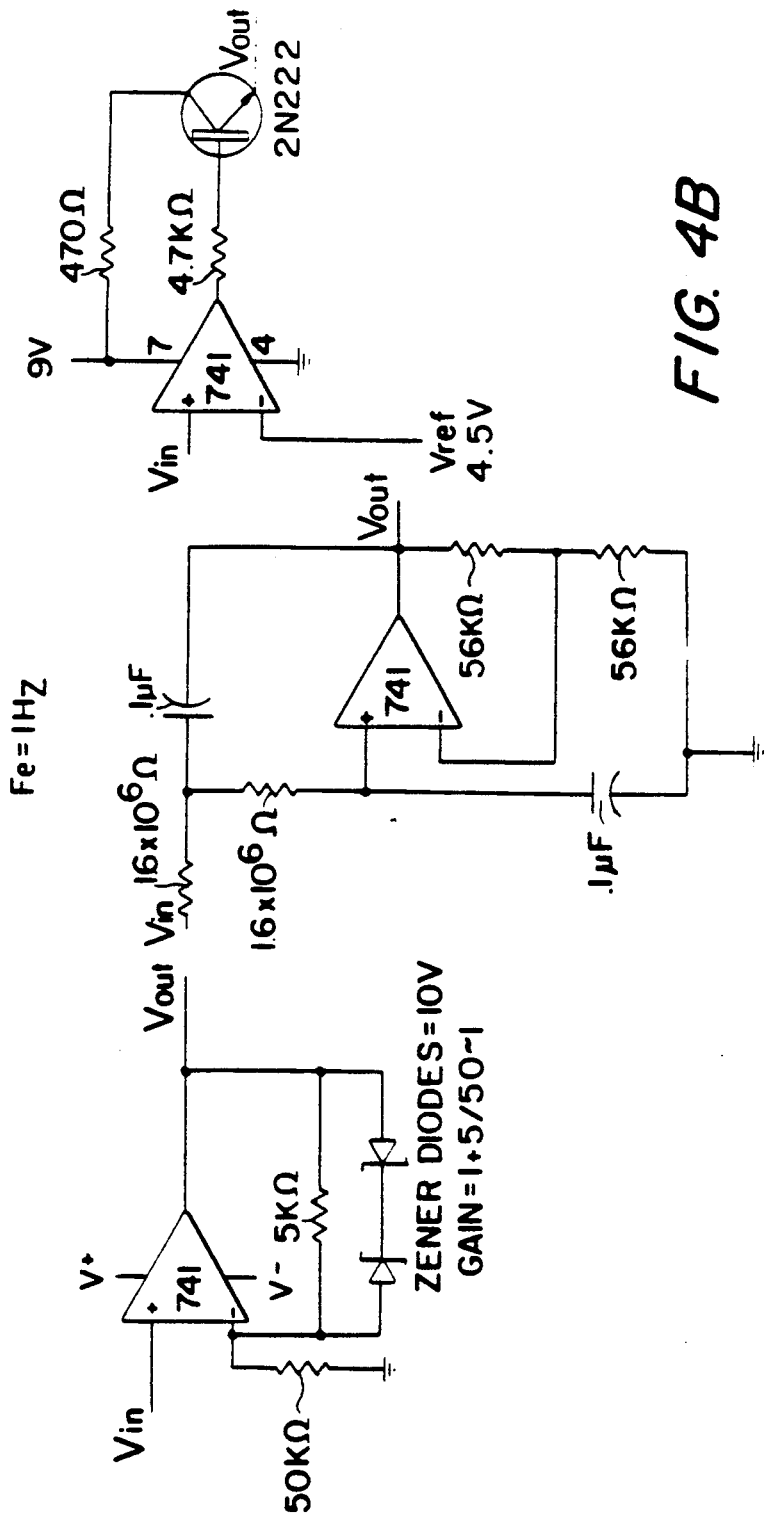

FIGS. 2 and 3 are graphic representations of the signals generated by the above-described piezo film sensor. In FIG. 2, the data was recorded at five samples per second. FIG. 2 shows the voltages generated by the sensor as the article with the sensor was handled, placed between the lips, drawn upon, and removed. This pattern of activity was repeated two additional times to create the three spikes seen in FIG. 2 at approximately 7 seconds, 12 seconds, and 18 seconds. The initial handling of the cigarette created the small peak at approximately 4 seconds. Following the above-described sequence of activity, the cigarette was again handled with the fingers to create the smaller peaks shown at 22 and 24 seconds. FIG. 2 thus clearly demonstrates that simple handling of the article and sensor does not produce the high amplitude signal that is produced during the user's draw.

In this example, the effect measured by the sensor was in fact a pyroelectric effect. Piezoelectric sensors are also good pyroelectric sensors. Here, the sensor was reacting to the change from room temperature (approx. 75° F.) to lip/mouth temperature (approx 98° F.).

In FIG. 3, the smoking article described above was first moved to the mouth, drawn upon, and then removed. This sequence was repeated two additional times. The signals generated can be seen in FIG. 3 at 3 through 9 seconds. The smoking article was afterward simply held between the lips (at 9 through 12 seconds), and then drawn upon four times (at 12 through 17 seconds), without removal of the article from the user's mouth. As exhibited in this range of the graph, the signals generated by the drawing action are significantly different than those generated by merely holding the smoking article between the lips.

Next, the smoking article was held between the lips while talking (at 18 through 25 seconds), and finally another series of draws were taken (at 26 through 30 seconds), with the smoking article removed from the mouth after each draw. Again, the signals generated by drawing were significantly stronger and sharper than those generated by talking.

A control system embodied within the overall sensor system may be used to differentiate between the above-exhibited draw and non-draw, or true and false, signals. The control system can thus reduce or eliminate the chance that the heating sequence be falsely or prematurely activated. The signal generated by the lip sensor is first passed through the control system. The system is circuited such that it will only produce an active output signal in response to a true draw signal. Only such an active output signal will trigger the heater activation control system.

FIG. 4 depicts a functional block diagram and corresponding circuit-level schematics. The circuit-level diagrams of the figure are presented such that each subsystem of the circuit is directly under that portion of the functional block diagram with which it corresponds. Each of the below-described subsystems are, as individual and isolated systems, known in the art. A person skilled in the art could design a circuit to accomplish each of the subsystem functions. The circuit-level diagrams and the values assigned to the components therein thus represent only preferred embodiments of the invention, and are meant to be illustrative, but not limiting.

Referring now to the figure, there is depicted a control system that includes several subsystems connected in series. The first subsystem is the lip sensor 11, as described above. The lip sensor generates an electric signal in response to user lip activity.

The second subsystem is a signal limiter circuit 12 used to block out signals above a certain level to protect the circuit components. Although not shown on the graphs in FIGS. 2 and 3, the piezo sensor can generate high voltage/high frequency signals that could damage the circuit components, if not blocked out. This signal limiter function can be accomplished by either of the circuits 12 in FIG. 4A, a signal divider and diode, or FIG. 4B, a signal follower.

The third subsystem is a lowpass filter circuit 13 used to eliminate signals above a chosen cutoff frequency. The piezo films in some cases generate many spurious signals, and these can be eliminated by allowing only lower frequency signals to pass through to the rest of the circuit. For purposes of this invention, the signals of interest would not usually have frequencies above 100 cycles per second. The lowpass filter function can be accomplished with the circuits as depicted in the figure.

The fourth subsystem is a threshold circuit 14 used to produce a signal only in response to an incoming signal of at least a preselected threshold value. This subsystem reduces or eliminates the low frequency and low amplitude signals that might be associated with non-draw activity, e.g., finger handling of the piezo sensor. This threshold function can be accomplished with a conventional Schmitt Trigger 14(A). The Schmitt Trigger is "triggered," and produces an output signal, only in response to an incoming signal of a preselected threshold value.

This threshold function may also be accomplished with the comparator circuit (FIG. 4B), wherein the incoming signal is compared with a reference signal, and an output signal is produced only if the incoming signal exceeds a preselected threshold value. For example, FIG. 2 shows signals produced from a user's draw that exceed +6 volts. If the reference signal were set at +6 volts, the lower amplitude signals due to finger handling would be eliminated. A pulse generator may be incorporated into either the comparator or Schmitt Trigger circuits in order to provide the output signal power to drive relays or other circuits as needed to trigger the heater activation control system.

Figure 5:
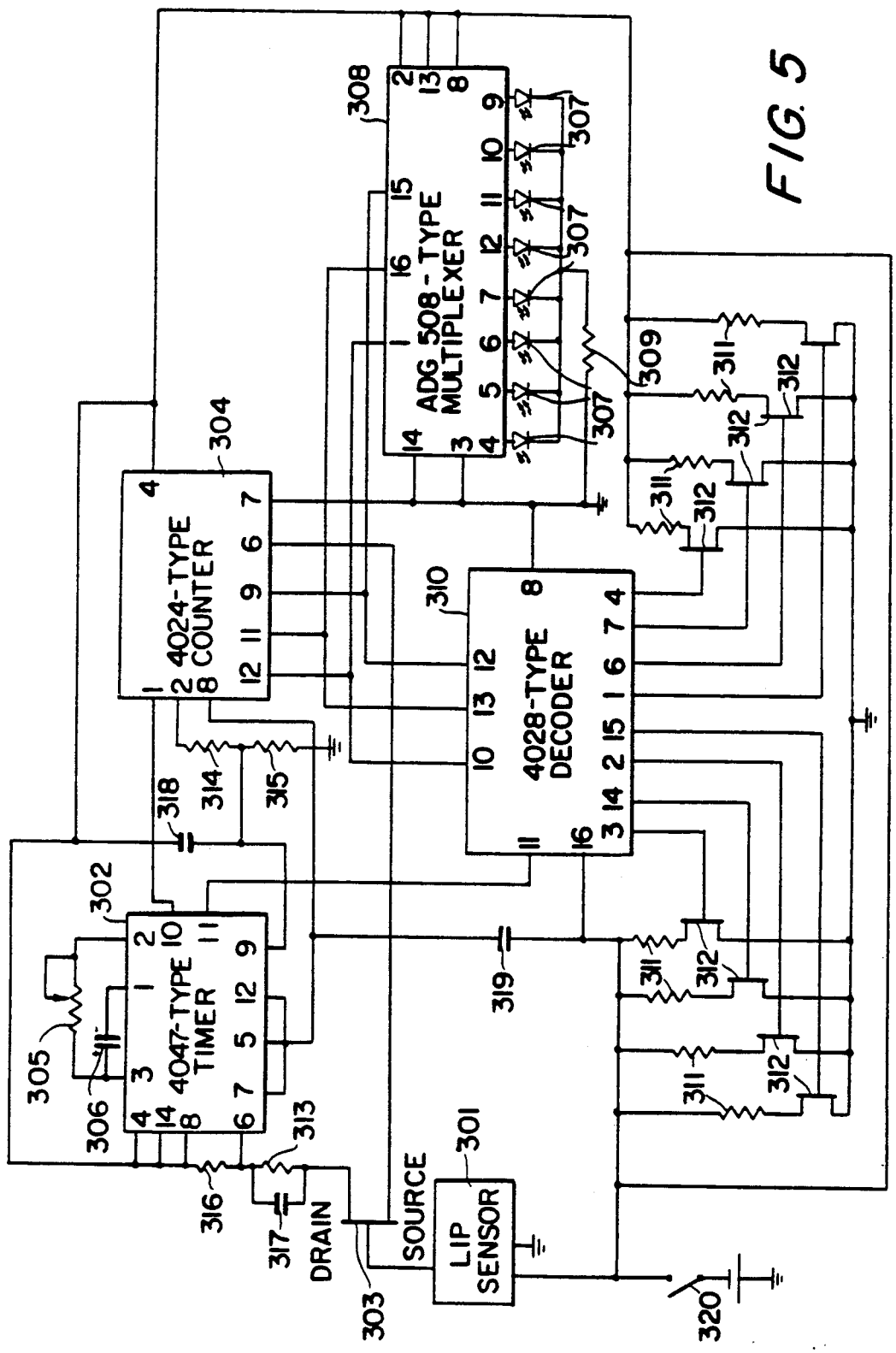
FIG. 5 is a schematic diagram of a heater activation control system.

If the signal is tested and determined to be a true draw signal, it is passed on to the heater activation control system. One embodiment of such a heater activation control system is depicted by the schematic diagram in FIG. 5. In that figure, a piezoelectric sensor 301 is placed at the tip of the mouthpiece of the flavor generator (not shown). The sensor is connected to a timer 302 which controls the heating of the flavor-generating material. The sensor 301 has two power inputs ($V_+$ and ground) and one output. The output drives the gate of MOSFET switch 303. The source of MOSFET switch 303 is connected to counter 304 (at pin 6). The drain of MOSFET switch 303 is connected through an RC circuit (resistor 313 and capacitor 317) to timer 302 (at pin 6).

A standard 4047-type timer 302 in a monostable configuration is connected to $V_+$ (via pins 4, 8, and 14) and to ground (via pins 5, 7, 12, and [9]) for negative triggering (through pin 6). Negative triggering is accomplished by first maintaining pin 6 positive, and then briefly pulling it to ground. This initiates the flavor-generating sequence. When triggered, the complementary timer outputs (via pins 10 and 11) change for a period of time dependent upon the resistance value R of variable resistor 305 (preferably 2MΩ, connected between pins 2 and 3) and the capacitance value C of capacitor 306 preferably 1 μF, connected between pins 1 and 3).

A standard 4024-type CMOS counter 304 is connected to $V_+$ (via pin 14) and to ground (via pins 8 and 7), and receives a positive clock pulse from timer 302 (via pin 1). Counter 304 is reset to 0 via a positive pulse through pin 2. BCD output is provided at pins 12, 11, 9 and 6. Each time the timer clock pulse (received at pin 1) changes from positive to ground, counter 304 advances one count. Counter 304 counts positive clock pulses and converts the count to BCD. Output pin 6 of the counter is connected to pin 6 of the timer 302.

Heater-active indicators 307 (light emitting diodes (LEDS) or other indicator devices) are connected to $V_+$ through an ADG508-type multiplexer 308 (via pins 4, 5, 6, 7, 12, 11, 10 and 9) made by Analog devices of Norwood, Mass. LEDs 307 are connected to ground via a 2 kΩ current-limiting resistor 309. Multiplexer 308 is connected to $V_+$ (via pins 1, 16 and 15). Multiplexer 308 receives BCD input from counter 304 and decodes it such that an individual output is selected through which $V_+$ is supplied to the LEDS.

Each of heaters 311 is connected to ground through a field-effect transistor (FET) 312. A particular FET will turn on under control of a standard 4028-type CMOS BCD to decimal decoder (via pins 3, 14, 2, 15, 1, 6, 7 and 4). Decoder 310 is also connected (via pin 11) to the complementary output of a timer 302 (also via pin 11). Pin 11 of decoder 310 is high when the output of timer 302 (pin 10) is low. All outputs of decoder 310 remain low if a BCD code greater than or equal to 1001 is applied through its inputs. Therefore, an output of decoder 310 can only be on during a positive clock pulse to counter 304. Decoder 310 will decode a standard BCD 4-bit code input from counter 304 into 1-of-10 outputs. Decoder 310 is connected to supply voltage $V_+$ (at pin 16) and to ground (at pin 8). Decoder 310 receives BCD input from counter 304 (at pins 10, 13 and 12).

Resistor 313 preferably has a value of 1MΩ, while resistors 314, 315 and 316 preferably each have values of 100MΩ. Capacitors 317 and 318 preferably each have values of 0.1 μF.

Prior to the user's initial draw, the control circuitry is turned on via on/off switch 320, or a similar device. The heater-active indicator LED is illuminated for the first heater 311. Correspondingly, heater number 1 is selected by decoder 310 and awaits firing. Counter 304 is reset to begin counting. Timer 302 complementary output at pin 10 (which is the clock to counter 304, pin 1) is low and at pin 11 is high. This keeps the heater from firing via pin 11 of decoder 310. When there occurs user draw lip activity, the lip sensor 301 causes triggering of timer 302. The RC time constant is determined by resistor 313 and capacitor 317 such that a pulse of desired duration is output from complementary outputs of timer 302. Those outputs, connected to pin 11 of decoder 310, go low, causing the first heater to be heated. The output at pin 11 returns to high, discontinuing heater activation. Since the count of counter 304 has advanced by one, the heater active LED selected by multiplexer 308 has correspondingly advanced, and the next heater to be fired in sequence has been selected via decoder 310. This cycle can be repeated until the final heater has been activated. At such time, pin 6 of the counter will go high causing timer 302, to become non-triggerable. In such case, the heater firing sequence is halted until the circuit is reset.

To further reduce the chance that the smoking article might be falsely or prematurely activated, it is possible to design the control device such that two or more separate signals are required to trigger the heating of the flavor-generating material. For example, two separate sensors, one which measures lip pressure and a second which measures air flow, could be used. In this case both the pressing of the user's lips against the mouthpiece and the drawing in of air would be required to trigger heating of the flavor-generating material. This type of control strategy would prevent a misfire in the case where pressure is accidentally applied to the mouthpiece by a source other than the user's lips, or in the case where the user is interrupted in the process of taking a draw, at a point after having applied pressure with his or her lips, but before drawing air through the flavor generator. It would also prevent the firing of the device by a change in air flow alone.

Figure 6:
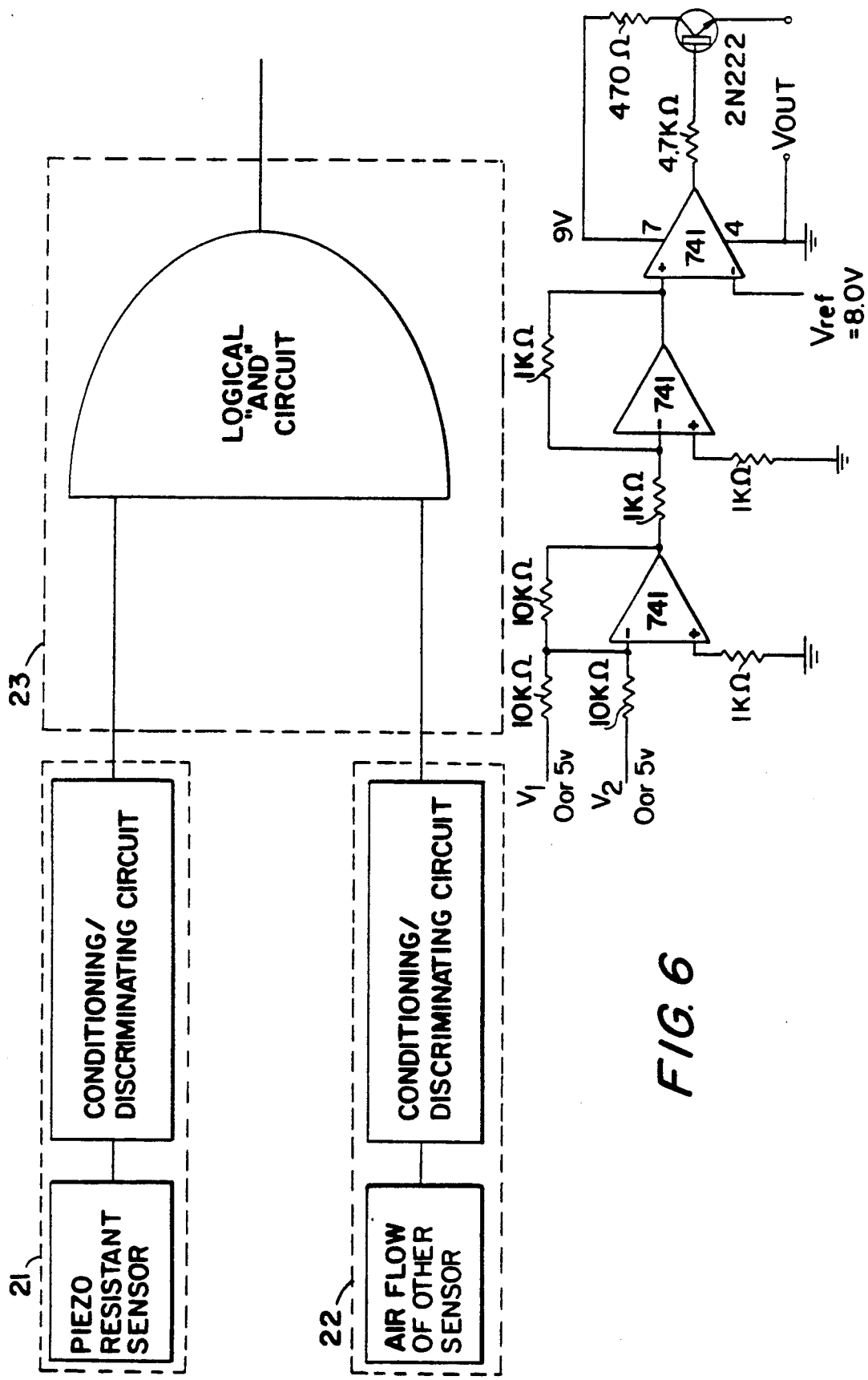
FIG. 6 is a functional and circuit-level diagram of a control system that uses in it at least two sensors.

Referring now to FIG. 6, there is depicted a functional block diagram and circuit-level schematic of one such control system. The control system itself includes three subsystems. The first subsystem 21 includes a sensor and signal conditioning/ discriminating circuitry. In that first subsystem, a lip sensor is used to detect draw activity and to produce a corresponding signal. That signal is passed through conditioning/discriminating circuitry, like that shown in FIG. 4, to discriminate between true and false draw signals, and to produce a corresponding logic signal of 0 V, false, or 5 V, true. The second subsystem 22 also includes a sensor and signal conditioning/discriminating circuitry, and produces a logic signal 0 V, corresponding to a false signal, or 5 V, corresponding to a true signal. The second subsystem preferably includes a sensor of a different type than that used in subsystem 21, since the use of dissimilar sensors should reduce the possibility of false signals derived from a single cause.

The third subsystem is a logical "AND" circuit 23 having as its inputs the logic signals from each of the two subsystems described above. The "AND" circuit produces a definite output pulse when and only when there is a HIGH pulse at the inputs from each of two sensors. This system only activates heating of the parent device when true draw signals are produced by both sensors, and thus reduces the likelihood of a false triggering of the device.

The use of three or more sensor subsystems should further reduce the likelihood of system misfire. The grouping of more than two sensors could be accomplished by constructing additional "AND" gates with the addition of new sensors.

The logical "AND" function can be accomplished with the corresponding circuit 23(a) as shown in the figure. In this circuit, an operational amplifier in summing mode combines the two signals, and thereafter feeds a comparator. The comparator is set with a reference above the value for one signal, and thus only produces an active output signal if it is fed with the sum of two sensor signals. The logical "AND" function can also be accomplished with several other well-known circuit arrangements. A pulse generator may be incorporated into this system in order to produce an output pulse with enough power to drive relays or other circuits as needed to trigger the parent device.

Other combinations of sensors are possible. The pressure sensor can be combined with an electrochemical sensor such that the sensor will only fire when the mouthpiece is in contact with the user's lips and pressure is applied by the lips. It is even possible to design a device which monitors multiple parameters, such as lip pressure, electrochemical potential at the lips, changes in electrical potential at the lips caused by contraction of the muscles, and air flow through the flavor generator. In this last embodiment, only when all the parameters indicate that the user is starting to draw will the heating of the flavor-generating material be triggered.

To reduce the lag time in a device using the dual sensor control system described above, the lip sensor may be used to activate all elements necessary for the heating of the flavor-generating material short of actually heating the material. This strategy reduces the processing time once the user starts to draw air into the mouth. In other words, one of the sensors could be monitored to "wake up" the system, and thus reduce power drain when the system is not being used. Alternatively, the lip sensor may begin to heat the flavor-generating material at a low energy level so that only a portion of the flavor is released. Then, when the user draws air through the flavor generator, additional power is supplied to the heater causing the release of the remaining flavor materials. In this latter embodiment, the user will receive a low level of flavor when he first starts to draw air, and that flavor will grow stronger as the draw continues. This system more closely approximates the sensation a user experiences when he smokes a conventional cigarette.

It may also be possible to design a control device which can be programmed by the user to respond to his particular draw behavior.

Thus, the above-described control device for electrically heated flavor-generating articles reduces or eliminates the lag time between the start of a draw and the delivery of flavor to the user, and also reduces the possibility of a misfiring of the flavor-generating sequence. One skilled in the art will appreciate that the present invention can be practiced by other than the described embodiments. The described embodiments are thus presented for purposes of illustration, and not of limitation.

I claim:

1. A lip sensor for an electric flavor generator, comprising:
   means for monitoring user lip activity provided at an end of the electric flavor generator such that during use it comes in physical contact with the user's lips; and
   means for producing an electric signal that corresponds to such activity, whereby the electrical signal produced in response to user draw lip activity differs from the electric signal produced in response to the user non-draw lip activity.

2. A control device for an electric flavor generator, comprising:

means for monitoring user lip activity provided at an end of the electric flavor generator such that during use it comes in physical contact with the user's lips; and means for producing a first electric signal that corresponds to such activity, whereby the electric signal produced in response to user draw lip activity differs from the electric signal produced in response to the user non-draw lip activity;

means for producing a second electric signal only when such first electric signal corresponds to user draw lip activity; and means for electrically heating a flavor-generating material in response to such second electrical signal.

3. The control device of claim 2 wherein the third means is an electric control circuit.

4. The control device of claim 3 wherein the electric control circuit is a threshold circuit.

5. The control device of claim 3 wherein the electrical control circuit comprises a lowpass filter circuit connected in series with a threshold circuit.

6. The control device of claim 3 wherein the electric control circuit comprises a signal limiter circuit connected in series with a threshold circuit.

7. The control device of claim 3 wherein the electric control circuit comprises a signal limiter circuit, a lowpass filter circuit, and a threshold circuit, all connected in series.

8. The control device of claims 4, 5, 6, or 7 wherein the threshold circuit is a Scmitt Trigger.

9. The control device of claims 4, 5, 6, or 7 wherein the threshold circuit is a comparator.

10. The control device of claims 6 or 7 wherein the signal limiter circuit is a signal divider and diode.

11. The control device of claims 6 or 7 wherein the signal limiter circuit is a signal follower.

12. The lip sensor of claim 1 wherein the means for monitoring user lip activity is a pressure sensor.

13. The lip sensor of claim 12 wherein the pressure sensor is piezoelectric film.

14. The control device of claim 2 wherein the means for monitoring user lip activity is a pressure sensor.

15. The control device of claim 14 wherein the pressure sensor is piezoelectric film.

16. The lip sensor of claim 1 wherein the means for monitoring user lip activity is a temperature sensor.

17. The lip sensor of claim 16 wherein the temperature sensor is piezoelectric film.

18. The control device of claim 2 wherein the means for monitoring user lip activity is a temperature sensor.

19. The control device of claim 18 wherein the temperature sensor is piezoelectric film.

20. The lip sensor of claim 1 wherein the means for monitoring user lip activity is an electric voltage sensor.

21. The control device of claim 2 wherein the means for monitoring user lip activity is an electric voltage sensor.

22. The lip sensor of claim 1 wherein the means for monitoring user lip activity is an electric current sensor.

23. The control device of claim 2 wherein the means for monitoring user lip activity is an electric current sensor.

24. The lip sensor of claim 1 wherein the means for monitoring user lip activity is an electrochemical sensor.

25. The lip sensor of claim 24 wherein the electrochemical sensor is a pH sensor.

26. The lip sensor of claim 24 wherein the electrochemical sensor is an ion level sensor.

27. The control device of claim 2 wherein the means for monitoring user lip activity is an electrochemical sensor.

28. The control device of claim 27 wherein the electrochemical sensor is a pH sensor.

29. The control device of claim 27 wherein the electrochemical sensor is an ion level sensor.

30. A control device for an electric flavor generator comprising:

means for sensing user lip activity;

means for producing a first electric signal that corresponds to such lip activity;

mean for converting the first signal to a digital HIGH, or 1, signal only when such first signal corresponds to user lip activity that is associated with taking a draw on the flavor generator;

means for sensing a flow of air through the flavor generator;

means for producing a second electric signal that corresponds to such air flow;

means for converting the second signal to a digital HIGH, or 1, signal only when such second signal corresponds to air flow that is associated with taking a draw on the flavor generator;

means for producing a third electric signal only when both the first digital signal and second digital signal are HIGH; and means for electrically heating a flavor-generating material in response to such third electric signal.

31. The control device of claim 30 wherein the third and sixth means include threshold circuits.

32. The control device of claim 30 wherein the means for producing the third electric signal is a logical "AND" electric circuit with the digital signals connected at its inputs.

33. The control device of claim 30 wherein the means for sensing lip activity is piezoelectric film.

34. The control device of claim 30 wherein the means for sensing a flow of air is a pressure-sensitive sensor.

35. The control device of claim 30 wherein the means for sensing a flow of air is a flow-sensitive sensor.

36. A control device for an electric flavor generator comprising:

two or more means for sensing user lip activity;

two or more means for producing electric signals that correspond to such activity;

two or more means for converting such electric signals to digital HIGH, or 1, signals only when such electric signals correspond to user activity that is associated with taking a draw on the flavor generator;

means for producing a final electric signal only when all digital signals are HIGH; and means for electrically heating a flavor-generating material in response to such final electric signal.

37. The control device of claim 36 wherein at least one of the means for sensing lip activity is piezoelectric film.

38. The control device of claim 36 wherein the means for producing the final electric signal is a logical "AND" electric circuit with the digital signals connected at its inputs.

39. A control device for an electric flavor generator comprising:

means for sensing user lip activity;
means for producing a first electric signal that corresponds to such activity;
means for sensing a flow of air through the flavor generator;
means for producing a second electric signal that corresponds to such air flow;
means for supplying electrical energy to heat a flavor-generating material in response to the first electric signal; and
means for supplying additional electrical energy to heat the flavor-generating material in response to the second electric signal.

40. The control device of claim 39 wherein the means for sensing lip activity is piezoelectric film.

41. A control device for an electric flavor generator comprising:
means for monitoring user lip activity;
mean for producing a first electric signal that corresponds to such activity;
means for producing a second electric signal only when such first electric signal corresponds to user draw lip activity;
means for sensing a flow of air through the flavor generator;
means for producing a third electric signal that corresponds to such air flow;
means for supplying electrical energy to heat a flavor-generating material in response to the second electric signal; and
means for supplying additional electrical energy to heat the flavor-generating material in response to the third electric signal.

42. The control device of claim 41 wherein the means for monitoring user lip activity is piezoelectric film.

43. The control device of claim 41 wherein the means for producing a second electric signal is an electric control circuit.

44. The control device of claim 43 wherein the electric control circuit comprises a threshold circuit.

45. The control device of claim 43 wherein the electric control circuit comprises a lowpass filter circuit connected in series with a threshold circuit.

46. The control device of claim 43 wherein the electric control circuit comprises a signal limiter circuit connected in series with a threshold circuit.

47. The control device of claim 43 wherein the electric control circuit comprises a signal limiter circuit, a lowpass filter circuit, and a threshold circuit, all connected in series.

48. The control device of claims 39 or 41 wherein at least one of the means for supplying electrical energy to heat a flavor-generating material in response to a particular electric signal includes an electric heater activation control circuit, comprising:
means for selecting one of a plurality of charges of flavor-generating material; and
means, initiated in response to such particular electric signal, for applying a pulse of electrical energy to heat the selected one of the plurality of charges of flavor-generating material.

49. The control device of claims 2, 30, or 36 wherein the means for electrically heating a flavor-generating material in response to a particular electric signal includes an electric heater activation control circuit, comprising:
means for selecting one of a plurality of charges of flavor-generating material; and
means, initiated in response to such particular electric signal, for applying a pulse of electrical energy to heat the selected one of the plurality of charges of flavor-generating material.

50. The control device of claim 48 wherein the selecting means is automatic.

51. The control device of claim 49 wherein the selecting means is automatic.

52. The control device of claim 50 wherein the automatic selecting means selects each of the plurality of charges sequentially.

53. The control device of claim 51 wherein the automatic selecting means selects each of the plurality of charges sequentially.

54. The control device of claim 52 wherein the electric heater activation control circuit further comprises sequential indication means for indicating which of the plurality of changes is selected.

55. The control device of claim 53 wherein the electric heater activation control circuit further comprises sequential indication means for indicating which of the plurality of changes is selected.

56. The control device of claim 48 wherein the pulse applying means applies a pulse of a predetermined duration.

57. The control device of claim 49 wherein the pulse applying means applies a pulse of a predetermined duration.

58. The control device of claim 48 wherein the electric heater activation control circuit further comprises pulse indication means for indicating when the pulse is being applied.

59. The control device of claim 49 wherein the electric heater activation control circuit further comprises pulse indication means for indicating when the pulse is being applied.

60. The control device of claim 56 wherein the electric heater activation control circuit further comprises pulse indication means for indicating when the pulse is being applied.

61. The control device of claim 57 wherein the electric heater activation control circuit further comprises pulse indication means for indicating when the pulse is being applied.

62. The control device of claim 56 wherein the electric heater activation control circuit further comprises lockout means for disabling the pulse applying means for a predetermined period of time after an actuation thereof.

63. The control device of claim 57 wherein the electric heater activation control circuit further comprises lockout means for disabling the pulse applying means for a predetermined period of time after an actuation thereof.

64. The article of claim 41 wherein the means for monitoring user lip activity is provided at an end of the electric flavor generator such that during use it comes in physical contact with the user's lips.

65. The control device of claims 30, 36, or 39 wherein the means for sensing user lip activity is provided at an end of the electric flavor generator such that during use it comes in physical contact with the user's lips.

* * * * *